(12) United States Patent
Horsmon et al.

(10) Patent No.: US 8,882,085 B1
(45) Date of Patent: Nov. 11, 2014

(54) MICRO ATOMIZER

(75) Inventors: Michael S. Horsmon, Joppa, MD (US); Charles L. Crouse, North East, MD (US); Richard J. Kreis, Bel Air, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 337 days.

(21) Appl. No.: 13/557,897

(22) Filed: Jul. 25, 2012

(51) Int. Cl.
*B05B 7/00* (2006.01)

(52) U.S. Cl.
CPC .............. *B05B 7/0012* (2013.01); *B05B 7/0075* (2013.01)
USPC ............ 261/78.2; 261/76; 239/337; 239/367; 239/369; 239/398; 128/200.14

(58) Field of Classification Search
CPC ....................................................... B05B 5/032
USPC .................... 261/76, 78.2, DIG. 54, DIG. 56; 285/133.11; 239/8, 240–341, 344–372, 239/398–399, 403, 405–406, 418, 433, 239/734.5; 128/200.14–200.23
See application file for complete search history.

(56) References Cited

U.S. PATENT DOCUMENTS

| | | | | |
|---|---|---|---|---|
| 2,857,128 A * | 10/1958 | Stern | .............................. | 251/151 |
| 3,430,864 A * | 3/1969 | Soodak et al. | ................. | 239/424 |
| 3,550,858 A * | 12/1970 | Larrabee et al. | .............. | 239/338 |
| 3,831,843 A * | 8/1974 | Masai | ................................ | 239/8 |
| 4,125,225 A * | 11/1978 | Venghiattis | ................... | 239/338 |
| 4,330,490 A * | 5/1982 | Higgins | ........................... | 261/62 |
| 4,635,850 A * | 1/1987 | Leisi | ............................... | 239/119 |
| 4,787,404 A * | 11/1988 | Klosterman et al. | ........... | 134/198 |
| 5,256,352 A * | 10/1993 | Snyder et al. | ................. | 261/78.2 |
| 5,337,962 A * | 8/1994 | Erb et al. | ..................... | 239/424.5 |
| 5,464,157 A * | 11/1995 | Bourdoulous et al. | ......... | 239/424 |
| 5,511,538 A * | 4/1996 | Haber et al. | .............. | 128/200.14 |
| 5,511,725 A * | 4/1996 | Barker et al. | ....................... | 239/8 |
| 5,513,798 A * | 5/1996 | Tavor | ................................. | 239/8 |
| 5,567,141 A * | 10/1996 | Joshi et al. | ........................ | 431/8 |
| 5,609,798 A * | 3/1997 | Liu et al. | ....................... | 261/78.2 |
| 6,076,748 A * | 6/2000 | Resch et al. | ................ | 239/424.5 |
| 6,166,379 A * | 12/2000 | Montaser et al. | ............. | 250/288 |
| 6,175,112 B1 * | 1/2001 | Karger et al. | .................. | 250/288 |
| 6,338,472 B1 * | 1/2002 | Shimazu et al. | .............. | 261/78.2 |
| 6,418,925 B1 * | 7/2002 | Genova et al. | ............ | 128/200.14 |
| 6,478,238 B1 * | 11/2002 | Wachs et al. | ................... | 239/338 |

(Continued)

FOREIGN PATENT DOCUMENTS

DE 3429411 A1 * 2/1986 ................ B05B 1/26

*Primary Examiner* — Duane Smith
*Assistant Examiner* — Stephen Hobson
(74) *Attorney, Agent, or Firm* — Ulysses John Biffoni

(57) ABSTRACT

A micro atomizer to produce stable aerosol concentrations having an aerosol mass median aerodynamic diameter (MMAD) of less than 10 microns with liquid flow rates in the microliter per minute range is provided. The micro atomizer includes a liquid channel in the shape of a thick-wall tube and a cap having an aerosol outlet orifice whereby a liquid-gas contact space is formed by the internal surface of the cap and the substantially flat end of the liquid channel. Pressurized carrier gas and the liquid to be aerosolized are allowed to come into contact within a precisely formed liquid-gas contact space. The desired aerosol characteristics are accurately established, stable, and reproducible. In an exemplary embodiment, the micro atomizer is used with a syringe and syringe drive to provide a continuous liquid source for aerosol generation.

9 Claims, 6 Drawing Sheets

(56) References Cited

U.S. PATENT DOCUMENTS

| | | | |
|---|---|---|---|
| 6,705,538 B2* | 3/2004 | Fecht et al. | 239/8 |
| 7,087,115 B1* | 8/2006 | Moein | 118/300 |
| 7,694,944 B2* | 4/2010 | Gottlieb et al. | 261/78.2 |
| 7,878,418 B2* | 2/2011 | Sevy | 239/8 |
| 7,886,990 B2* | 2/2011 | Scheer | 239/8 |
| 7,913,938 B2* | 3/2011 | Cooper | 239/690 |
| 8,057,220 B2* | 11/2011 | Bretz | 431/159 |
| 8,091,867 B2* | 1/2012 | Kikuchi et al. | 261/78.2 |
| 8,613,400 B2* | 12/2013 | Filicicchia et al. | 239/403 |
| 2005/0098655 A1* | 5/2005 | Reetz, III | 239/296 |
| 2007/0062518 A1* | 3/2007 | Geser et al. | 128/200.14 |
| 2008/0116594 A1* | 5/2008 | Williams | 261/78.1 |
| 2009/0051056 A1* | 2/2009 | Kikuchi et al. | 261/78.1 |
| 2010/0258648 A1* | 10/2010 | Filicicchia et al. | 239/4 |

* cited by examiner

MICRO ATOMIZER

GOVERNMENT INTEREST

The invention described herein may be manufactured, used, and/or licensed by or for the United States Government.

BACKGROUND

1. Technical Field

The present invention generally relates to the technical field of gas and liquid contact devices and methods to produce an aerosol, and, more particularly, to an atomizer for use in aerosol generation at continuous, but ultra-low liquid flow rates such as 50 microliters per hour. Accordingly, the device of the present invention is referred to herein as a micro atomizer.

2. Description of the Related Art

Research in inhalation toxicology requires the ability to generate stable aerosol concentrations of a respirable particle size in a consistent manner from day to day and experiment to experiment. Respirable, as used herein, refers to airborne particles capable of entering and depositing in the upper airways and the lower airways of the lungs. The upper airways include the trachea and the primary, secondary, and tertiary bronchus. The lower airways include the bronchioles, terminal bronchioles, and alveoli. Aerosol deposition in the upper airways of the human is generally achieved by a particle size between about 2.5 and 10 microns (μm) aerosol mass median aerodynamic diameter (MMAD) with the larger particles depositing in the larger airways. Aerosol deposition in the lower airways of the human is generally achieved between 0.5 and 2.5 μm MMAD with maximal alveolar deposition occurring with particles of about 1.2 μm MMAD or smaller. For inhalation studies using small research animals, the range for the upper airways is approximately 2.0 to 6.0 μm MMAD and for the lower airways 0.5 to 2.0 μm MMAD.

In addition to inhalation toxicology, other research areas in the life and physical sciences, various manufacturing processes, and certain systems or products have a need for precise and accurate atomization to produce aerosols having small particle size at low to ultra-low, yet stable, concentrations. Various methods of generating such aerosols are in use, but suffer from a number of limitations, some of which are described below. These methods depend on parameters such as the physical state of the material to be aerosolized, vapor pressure of the material to be aerosolized and physical parameters of the desired aerosol exposure to be achieved.

While several commercially available products exist for liquid aerosol generation, for the inhalation toxicology research that motivated the present invention, none were found that would function properly and consistently at the required ultra-low liquid flow rates ranging from microliters per minute to microliters per hour. Additionally, the materials used in the studies for which the micro atomizer herein was invented require that the atomizer be constructed of materials resistant to organic solvents and caustic solutions. These features also would be desirable or required for most of the other applications mentioned above.

By way of example, one prior art device and method to generate aerosol at the desired liquid flow rates utilizes a modified commercially available spray atomizer nozzle (Spraying Systems Co., pneumatic atomizer model 1/4 JSS). This atomizer nozzle was modified to improve its performance for the inhalation toxicology studies by changing the delivery means of the liquid to be aerosolized. In particular, the reservoir injection means was replaced with a syringe and a syringe drive to more precisely control liquid flow at low flow rates. In addition, the liquid stream was kept separate from the atomizing air stream until reaching the tip of the nozzle. These modifications allow for greater control over the flow of liquid in comparison to the unmodified, commercially available pneumatic atomizer. Through use of this modified device, both aerosol particle size and aerosol concentration can be adjusted by changing either the liquid flow rate through adjustment of the syringe drive or by changing the air flow rate and pressure using a commercially available mass flow controller or pressure regulator.

Despite these benefits, the modified, commercially available pneumatic atomizer suffers operational limitations as it is a relatively large piece of equipment requiring liquid flow rates in the milliliter per minute/hour range as well as an air flow rate on the order of 20 liters per minute. These parameters make this generation method appropriate when relatively large volumes of liquid are available and acceptable, high aerosol concentrations are desired, and the application involves in a relatively large aerosol chamber. The chambers used in the inhalation toxicology studies that motivated this invention, however, are small in comparison and cannot operate with a generation system that outputs more than 5 liters per minute of air.

A second prior art device used to generate aerosol at the desired liquid flow rates involves the use of what may be referred to as a double-needle atomizer. This device involves the use of two small pieces of stainless steel tubing, or two appropriately sized needles such that the smaller of the two needles fits within the larger with enough room or clearance that air can flow through the larger needle. These needles are connected to a manifold that allows air to enter the larger needle and liquid to enter the smaller needle. The smaller needle carrying the liquid to be aerosolized is connected to a syringe, which in turn is connected to a syringe drive. The tip of the smaller needle carrying the liquid is set to extend approximately 0.5 mm past the tip of the larger needle carrying pressurized air. When an air flow through the larger needle is of appropriate pressure and flow rate, the liquid exiting the smaller needle is aerosolized. By way of example, the smaller needle in this prior art device is typically a 32 gauge blunt ended needle and the larger needle is a 21 gauge blunt ended needle.

Limitations of this second prior art device involve its inconsistency and unreliability in generating the same aerosol characteristics from day to day. While the double-needle design is capable of working in the desired microliter per minute to microliter per hour range and generates low concentrations in small aerosol chambers, its design has inherent flaws that cause it to perform in an inconsistent manner. In particular, the liquid-gas contact space is variable in day-to-day operations. This can occur, for example, due to small changes in the location and orientation of the inner needle relative to the outer needle. Such changes in the shape of the liquid-gas contact space result in undesirable changes in aerosol characteristics.

Another prior art method involves the adaption of commercially available ink jet cartridges. While ink jet cartridges can be utilized to produce aerosols, the amount of liquid needed exceeds the desired flow rates for the applications described above.

Accordingly, there remains a need for a micro atomizer capable of generating aerosols at liquid flow rates in the microliter per minute range or lower in a reproducible and consistent manner. Such a device can be used for the inhalation toxicology studies that motivated this invention as well as other applications in the life and physical sciences, manufacturing, and systems or products that require or could benefit from a micro atomizer as described herein.

SUMMARY

In view of the foregoing, an exemplary embodiment of a micro atomizer to produce stable aerosol concentrations having MMAD values of less than 10 μm with liquid flow rates in the microliter per minute range is provided. The micro atomizer includes a liquid channel in the shape of a thick-wall tube and a cap having an aerosol outlet orifice whereby a liquid-gas contact space is formed by the internal surface of the cap and the substantially flat end of the liquid channel. Pressurized carrier gas and the liquid to be aerosolized are allowed to come into contact within a precisely formed liquid-gas contact space. The desired aerosol characteristics are accurately established, stable, and reproducible. In an exemplary embodiment, the micro atomizer is used with a syringe and syringe drive to provide a continuous liquid source for aerosol generation.

These and other aspects of the embodiment herein will be better appreciated and understood when considered in conjunction with the following description and the accompanying drawings. It should be understood, however, that the following descriptions, while indicating an exemplary embodiment and numerous specific details thereof, are given by way of illustration and not of limitation. Many changes and modifications may be made within the scope of the embodiment herein without departing from the spirit thereof, and the present invention includes all such modifications.

DETAILED DESCRIPTION

The embodiments herein and the various features and advantageous details thereof are explained more fully with reference to a non-limiting embodiment that is illustrated in the accompanying drawings and detailed in the following description. Descriptions of well-known components and processing techniques are omitted so as to not unnecessarily obscure the embodiment herein. The examples used herein are intended merely to facilitate an understanding of ways in which the embodiment herein may be practiced and to further enable those of skill in the art to practice the present invention. Accordingly, the examples should not be construed as limiting the scope of the present invention.

Figure 1:
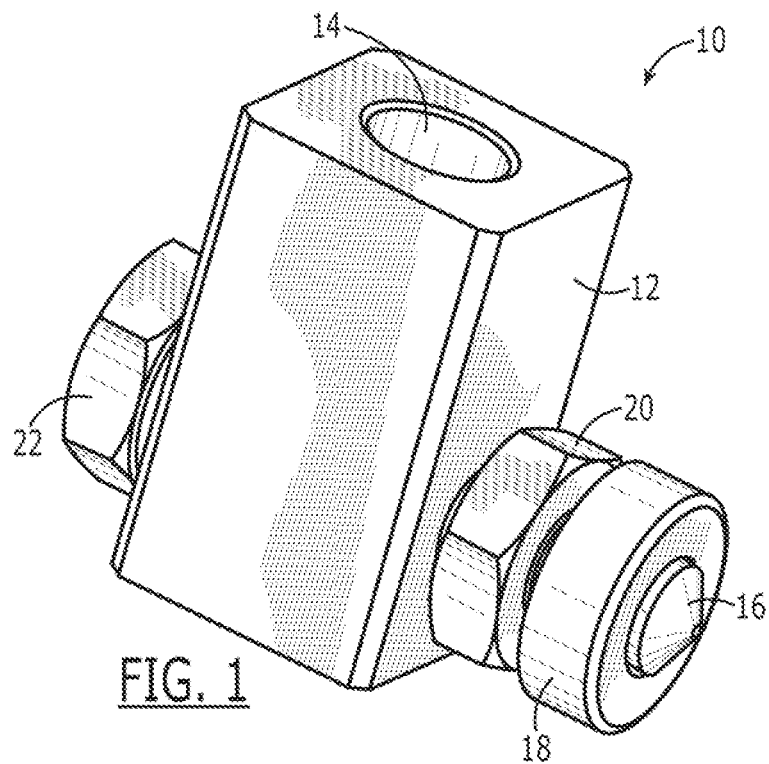
FIG. 1 is a first perspective view illustrating the outlet side of a micro atomizer according an exemplary embodiment of the present invention.

Turning to FIG. 1, a first perspective view is provided to illustrate the outlet side of a micro atomizer according to an exemplary embodiment of the present invention. Micro atomizer 10 includes body 12 having orifice 14 for connection to a source of pressurized air or an alternative carrier gas. Body 12 also includes orifices for receiving fittings 20 and 22. In the exemplary embodiment illustrated, body 12 was made from a stainless steel block with dimensions of approximately 1.5× 0.5×0.5 inches. The details of body 12 are illustrated and described below in reference to the cross-sectional views.

Returning to FIG. 1, fitting 20 is used with fitting 18 to fasten cap 16 to the assembly of micro atomizer 10. As described below in reference to the cross-sectional views, fitting 20 includes orifices for carrier gas flow and for housing a liquid feed channel. Fitting 22 is in the exemplary embodiment illustrated attached to body 12 on the opposite side as fittings 18 and 20, with all three fittings 18, 20, 22 and cap 16 arranged along a common centerline which passes through body 12.

In the exemplary embodiment illustrated, cap 16 and fittings 18, 20, and 22 are commercially available stainless steel fittings having threaded connectors. Such fittings are well known in the art of mechanical engineering and are available in a wide range of features and options. For example, such fittings are readily available in other metals and rigid plastics, and in different shapes and sizes. Body 12, cap 16, and fittings 18, 20, 22 may be made of an alternative material such as a ceramic or composite. In addition, two or more of these components can be combined in an alternative embodiment. For example, block 12 and fitting 22 may be machined, cast, or formed by various manufacturing means as a single part which performs the same or equivalent function as taught herein.

The materials selected to comprise micro atomizer 10 should be substantially impermeable and nonreactive to the liquids and air or other carrier gas to be used with the device, substantially rigid to maintain structural integrity and dimensional tolerances, and will resist cracking, corrosion, and other possible failure modes. Stainless steel component parts have been used for the exemplary embodiment described herein and provide these desired attributes.

Figure 2:
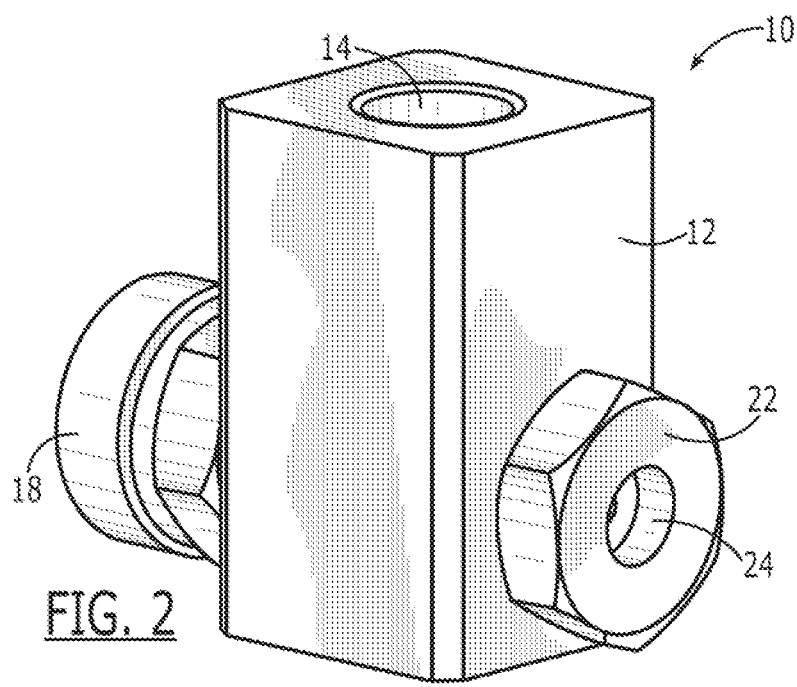
FIG. 2 is a second perspective view illustrating the syringe side of a micro atomizer according an exemplary embodiment of the present invention.

Turning to FIG. 2, a second perspective view is provided to illustrate the syringe side of a micro atomizer 10 according to an exemplary embodiment of the present invention. As previously shown, micro atomizer 10 includes body 12 having orifice 14 for connection to a source of pressurized air or an alternative carrier gas. Body 12 also includes orifices for receiving fittings 20 and 22. In this particular view, orifice 24, which is formed by fitting 22 is visible. Orifice 24 provides a means to attach a syringe (not shown) containing the fluid to be atomized. The attachment means between orifice 24 and the syringe should prevent leakage of fluid from the syringe. This may be accomplished using a threaded fitting, compression fitting, o-ring, or other means that are well known in the art. In the exemplary embodiment illustrated, this is accomplished with threaded fittings which mate to threads on a commercially available syringe.

Figure 3:
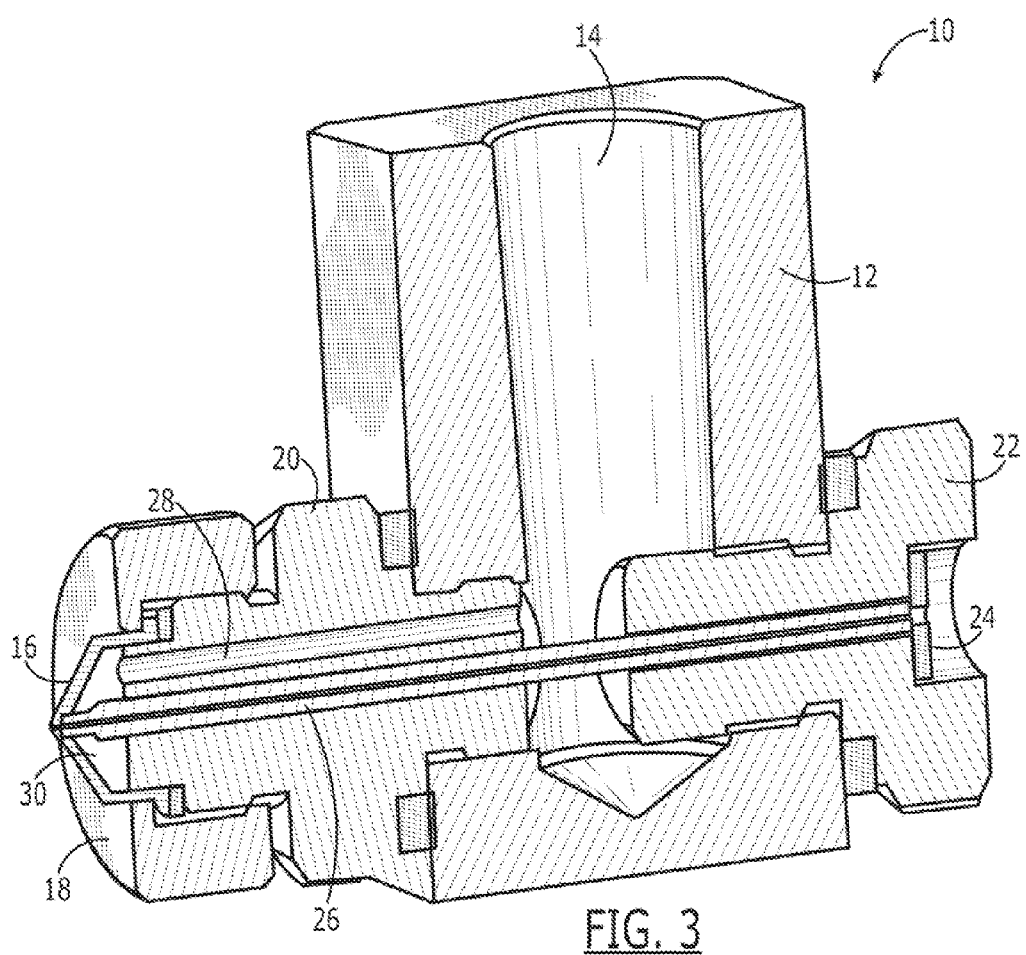
FIG. 3 is a cross sectional view illustrating internal parts and features of a micro atomizer according an exemplary embodiment of the present invention.

Turning to FIG. 3, a cross-sectional view is provided illustrating internal parts and features of micro atomizer 10 according to an exemplary embodiment of the present invention. The entire length of orifice 14 of body 12 is illustrated in this view along with the other two orifices of body 12 for receiving fittings 20 and 22. In addition, liquid channel 26 is visible in this view as is carrier gas channel 28. Liquid channel 26 is substantially a thick-wall tube with a small inner diameter of the channel in which the liquid flows and a relative stiffness to maintain its linear shape and position relative to cap 16. In the exemplary embodiment, commercially available stainless steel tubing of 0.062 inches outer diameter and 0.007 inches inner diameter was used for liquid channel 26 (McMaster Carr, stainless steel tubing). As illustrated in FIG. 3, liquid channel 26 substantially contained within fittings 20 and 22 and extends to the outlet area of cap 16. In the exemplary embodiment, liquid channel 26, is inserted into fitting 22 and soldered to fitting 22 to secure its position and orientation as well as to create a leak-tight seal. When fitting 22 is threaded into body 12, liquid channel 26 is thereby positioned precisely and accurately within the assembly of micro atomizer 10. By way of example, in the exemplary embodiment illustrated herein, the clearance dimension between the liquid channel 26 and cap 16 is approximately 0.001 inches radially. The precise (reproducible) and accurate control of the liquid-gas contact space results in a corresponding precise and accurate control of atomization performance.

Returning to FIG. 3, fitting 20 includes one or more carrier gas channels 28 for allowing carrier gas from a pressurized gas source (not shown) attached to orifice 14 to flow through fitting 20 and into the space formed by cap 16 and fitting 20. In the exemplary embodiment illustrated, three carrier gas channels 28 are provided which are symmetrically arranged relative to and parallel with the centerline of fitting 20. The same or similar function, however, could be accomplished with a single carrier gas channel, or some number other than three as described herein.

Figure 4:
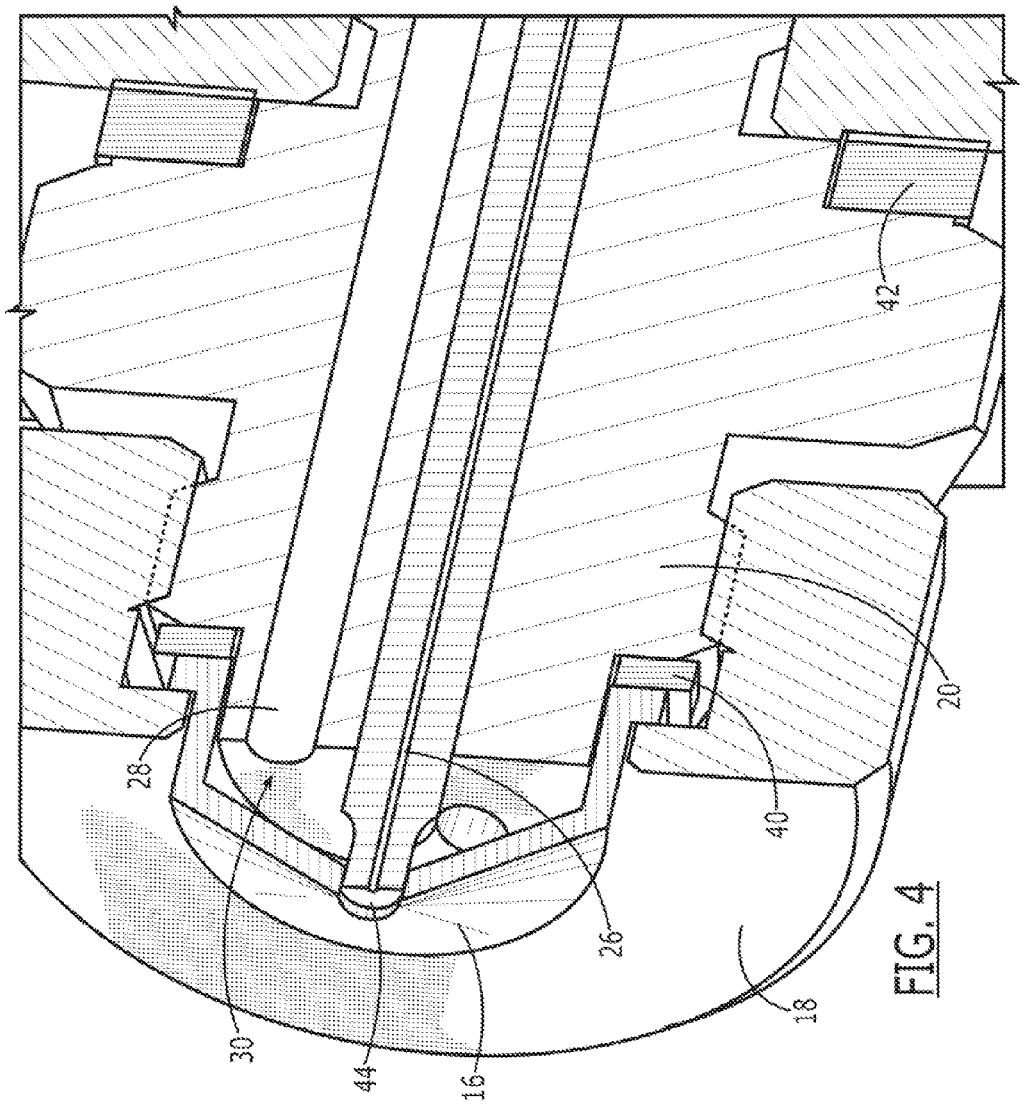
FIG. 4 is an enlarged detail of the cross sectional view further illustrating internal parts and features of the outlet components of a micro atomizer according an exemplary embodiment of the present invention.

Turning to FIG. 4, an enlarged detail of the cross sectional view is provided to further illustrate internal parts and features of the outlet components of a micro atomizer according to an exemplary embodiment of the present invention. In this view, the space 30 formed by cap 16 and fitting 20 is clearly visible. As illustrated in this particular embodiment, cap 16 is secured to fitting 20 by fitting 18. A gasket 40 is used in this exemplary embodiment for a leak tight seal of cap 16 throughout its contact area with fitting 20. Accordingly, the pressurized carrier gas within space 30 flowing from carrier gas orifices 28 can only escape through the orifice 44 of cap 16 where it comes in contact with fluid from liquid channel 26 to produce atomized liquid particles. Also shown in this view is gasket 42 which is used for a leak tight seal of fitting 20 into the body of the micro atomizer.

Figure 5:
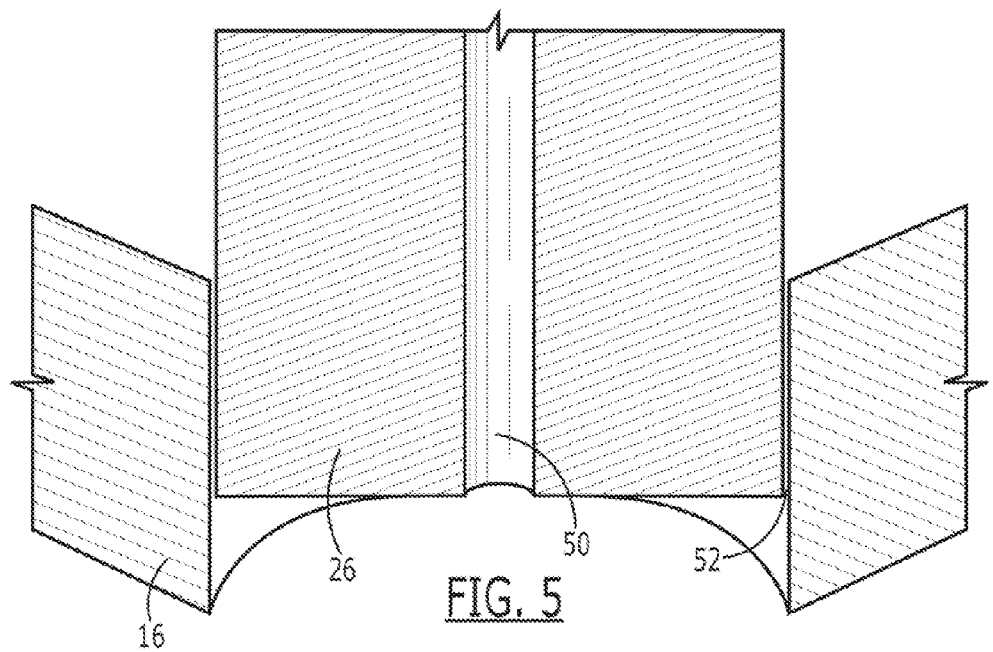
FIG. 5 is a further enlarged detail of the cross sectional view further illustrating internal parts and features of the outlet components of a micro atomizer according an exemplary embodiment of the present invention.

Turning to FIG. 5, a further enlarged detail of the cross sectional view of FIG. 4 is provided to further illustrate internal parts and features of the outlet components of an exemplary embodiment of the present invention. In this view, the shape of the thick-wall tube of liquid channel 26 is clearly illustrated, including its substantially flat end which fits within the orifice formed by cap 16. Liquid channel 26, in this exemplary embodiment, has an inner diameter of approximately 0.007 inches, which defines orifice 50 through which the liquid to be aerosolized flows. Clearance 52 between cap 16 and liquid channel 26, in this exemplary embodiment, is approximately 0.001 inches measured radially. That is, the gap between liquid channel 26 and cap 16 on each side as illustrated in this cross-sectional view is approximately 0.001 inches. The distance that cap 16 extends past the end of liquid channel 26 when fitting 18 is threaded completely into fitting 20 is approximately 0.005 inches in this exemplary embodiment. Those with Ordinary skill in the art will understand how these dimensions are readily adjustable to provide alternative spacing should it be desired. This can be accomplished as a one-time design change or as a user-adjustable feature.

The dimensions as described above allow pressurized carrier gas to flow through clearance 52 between liquid channel 26 and cap 16 with appropriate volume and pressure to interact with liquid flowing out of orifice 50. The dimensions and orientation of parts as taught herein with reference to this exemplary embodiment are readily achieved with tight dimensions and tolerances, which are reproducible over the entire service life of the micro atomizer, which may be years. Liquid-gas contact or interaction thus occurs in the cylindrical space formed by the orifice of cap 16 and the end of liquid channel 26 and projecting outward (or down in the orientation illustrated in FIG. 5) from the end of liquid channel 26. This small and controlled liquid-gas contact/interaction space produces the desired atomization results.

Neither the carrier gas source nor the liquid source are illustrated in the foregoing drawings as both are readily accomplished using commercially available products. Carrier gas, which can be air or another gas such as nitrogen, can be supplied from a standard laboratory pressurized air system, a pressure vessel or tank with regulator and hose or tubing, or other means such as a small pump. The present invention as taught in the embodiment illustrated is compatible with various liquid sources such as commercially available syringes and syringe drives. Syringe drives that can be used with the present invention include but are not limited to the Harvard Syringe Drive Model Number 55-2222, or equivalent. Syringes that may be used with the present invention include but are not limited to the Hamilton Microliter Series Gastight Syringe, the Harvard Stainless Steel Syringe, Beckton Dickinson Plastic Syringe, the Poper & Son Glass Syringe, or equivalent. In addition, other means to provide liquid to the micro atomizer are well known in the art or can be engineered using ordinary skill. An example of such an alternative fluid source is a fluid vessel with a pressurized head or pump such that liquid flows to a regulator which then feeds into the micro atomizer through a hose or tubing.

Having described the structural components and features of a micro atomizer with reference to an exemplary embodiment, along with some alternative embodiments, attention is now turned to a series of demonstration runs of the micro atomizer and the corresponding aerosol generation data thus produced. In this demonstration of performance characteristics, nine different combinations of carrier gas flow rate and feed rate were established. With the exception of run 1, which occurred at a pressurized gas source of 60 pounds per square inch (psi), runs 2-9 where at a pressurized gas source of 100 psi. For each combination, the resulting MMAD values and particle counts were measured. MMAD is commonly defined and used consistently herein as the diameter at which 50% of the particles 15" by mass are larger and 50% are smaller. For each demonstration run, the MMAD and particle count were measured in real time using an Aerosol Particle Sizer (APS), Model 3321 from TSI incorporated of Shoreview, Minn. Data representing one-minute averages were collected once per second using the APS. These data were exported to Microsoft Excel software for analysis and are presented in Table 1 below. Of note are the desirable ultra-low liquid feed rates of 10 to 1000 microliters per hour (µl/hr) and the desirable MMAD values of approximately 1 to 6 µm. It should also be noted that numerous combinations of carrier gas flow rate, liquid feed, and carrier gas pressure can be used to provide a variability or adjustability of MMAD and particle count. Particle count values are discussed below in reference to FIG. 7.

TABLE 1

Aerosol mass median aerodynamic diameters

| Run # | Carrier Gas Flow Rate (L/min) | Liquid Feed Rate (µl/hr) | Carrier Gas Source Pressure (psi) | Mean MMAD (µm) |
|---|---|---|---|---|
| 1 | 1.2 | 1000 | 60 | 5.31 |
| 2 | 1.5 | 1000 | 100 | 5.8 |
| 3 | 1.5 | 500 | 100 | 6.22 |
| 4 | 1.5 | 10 | 100 | 4.99 |
| 5 | 1.5 | 50 | 100 | 5.2 |
| 6 | 1.5 | 100 | 100 | 5.4 |
| 7 | 1.7 | 100 | 100 | 4.04 |
| 8 | 2 | 50 | 100 | 1.01 |
| 9 | 2 | 10 | 100 | 2.51 |

Figure 6:
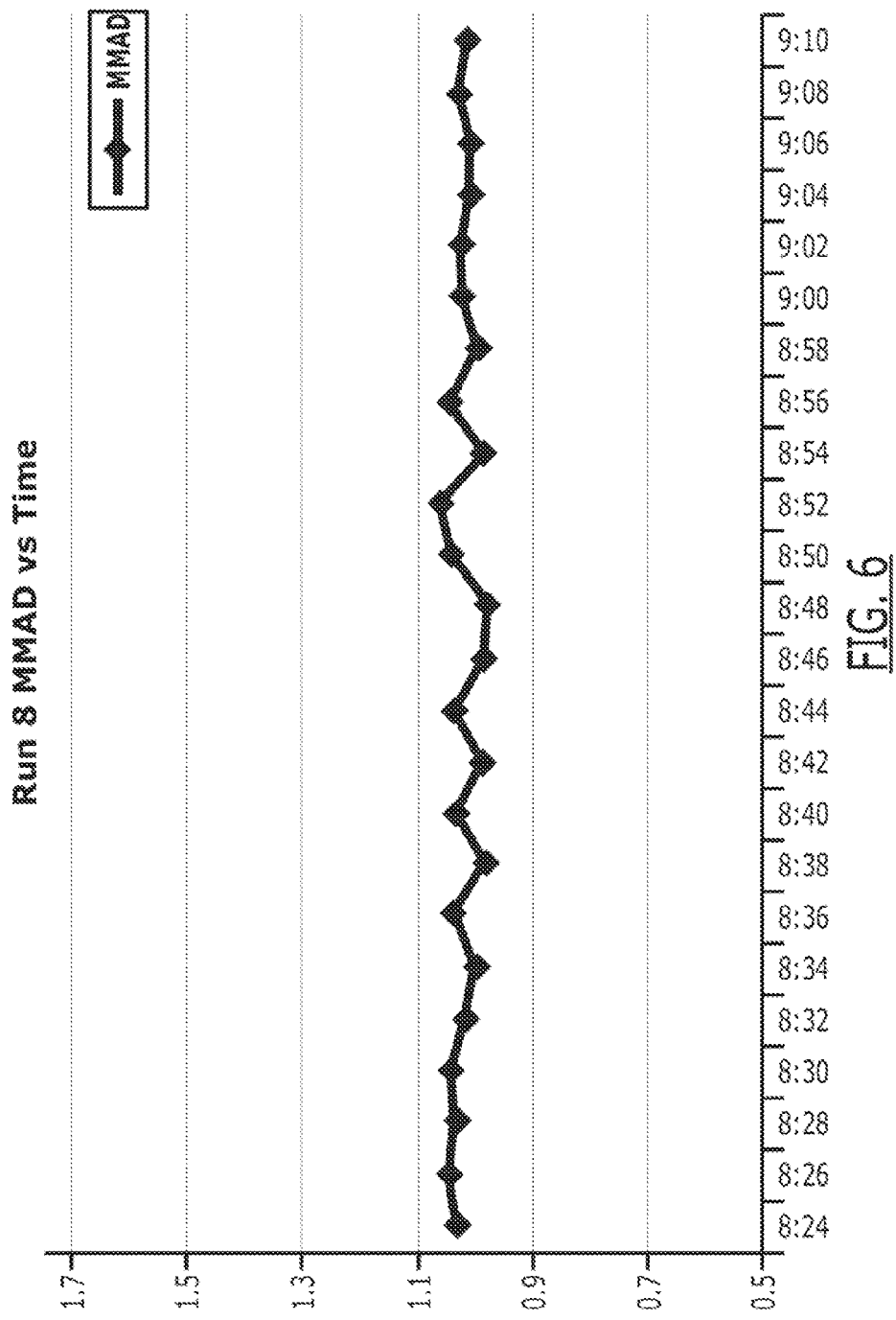
FIG. 6 is a graph of particle size as measured in a representative 45-minute demonstration run of a micro atomizer according an exemplary embodiment of the present invention.

Turning to FIG. 6, a graph of MMAD (particle size) as measured in a representative 45-minute demonstration run of the micro atomizer embodiment described herein is provided. In particular, these data are representative of micro atomizer performance under the conditions specified in Table 1 above for run number 8. Data representative of the other runs were graph similarly, but around a vertical axis value corresponding to the mean MMAD value in Table 1. As illustrated in the plot of FIG. 6, the particle sizes produced by the exemplary micro atomizer taught herein, and under the conditions listed for run number 8 in Table 1, are tightly controlled within 0.9 and 1.1 µm with a mean M MAD of 1.01 µm. That is a noteworthy performance outcome which is desirable for certain applications as described herein. In addition, the liquid feed rate was a mere 50 µl/hr, which again, is desirable for certain applications as described herein.

Figure 7:
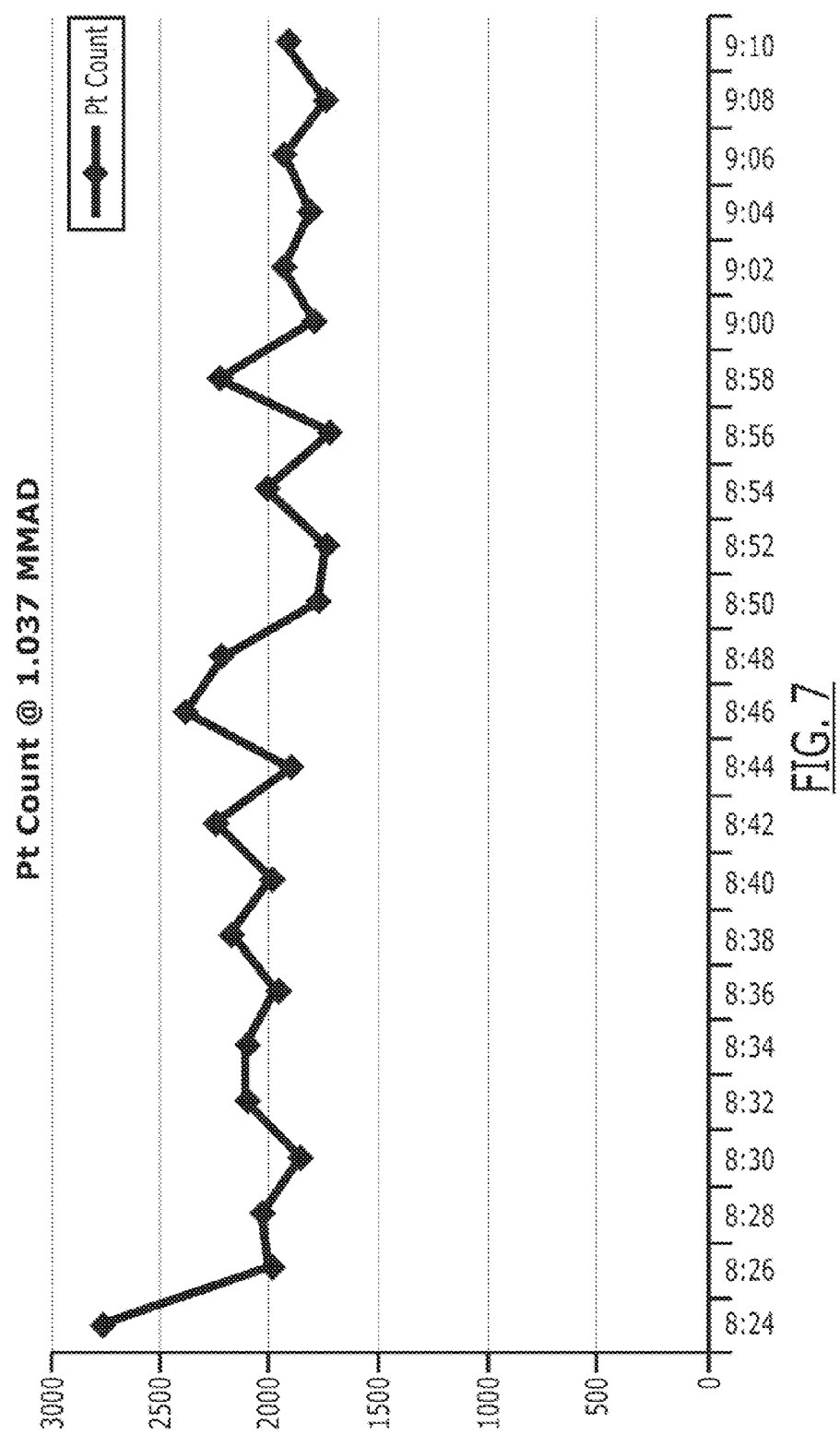
FIG. 7 is a graph of particle count of the aerosol produced in a representative 45-minute demonstration run of a micro atomizer according an exemplary embodiment of the present invention.

Turning to FIG. 7, is graph of particle count of the aerosol produced in a representative 45-minute test or demonstration run of the micro atomizer embodiment described herein is provided. As illustrated, this particle count corresponds to a MMAD of 1.037 µm, and with only one outlying data point, stays within 1500 to 2500 counts per second. The APS identified above, was used to measure the number of particles of a given size range per second of real time monitoring. Corn oil was used as the material for this demonstration run.

If desired, real-time monitoring of particle count using the APS instrument, or equivalent, can be correlated with a concentration expressed in units such as milligrams per cubic meter (mg/m3). This can be accomplished using a standard gas chromatography/mass spectrometer (GC/MS) to perform analyses of aerosol samples collected on a filter pad. Such methods and instrumentation are well known in the art. The correlation between APS real-time particle count data and concentration data as measured with a GC/MS and filter-pad collection method may differ for different liquids aerosolized because the counting process is based on laser diffraction or reflectivity and liquids of different material or composition will have different laser diffraction and reflectivity characteristics. The particle counts achieved in the demonstration run illustrated here would likely result in aerosol concentration data as measured with a GC/MS and filter-pad collection method within the range of 1 to 10 mg/m3. Such a range is well suited for inhalation toxicology studies as well as other purposes.

The various performance characteristics described above are particularly useful in the inhalation toxicology studies which motivated the invention. In addition to inhalation toxicology, the micro atomizer could be used in other applications where there is a need for atomization at stable aerosol concentrations of small particle size at low to ultra-low concentrations. This could include other research or experimental applications in the life and physical sciences, various manufacturing processes, and certain systems or products that require atomization.

While a specific exemplary embodiment of the invention has been described, it will be understood that additional embodiments and various modifications may be made without departing from the spirit and scope of the invention. For example, the dimensions of the present invention and its component specifications can be adjusted and optimized for various applications. The size, shape, and type of fittings, for example, may vary for alternative embodiments. The size and shape of the body may vary for alternative embodiments while accomplishing the same function. The body and one or more fittings can be combined into a single part. The shape and path of the carrier gas and fluid channels can vary as well. More than one fluid channel can be used. Rather than multiple air channels as taught in the exemplary embodiment herein, a single air channel, two channels, or a plurality of channels can be used to deliver pressurized carrier gas to the fluid-gas contact space. Components of the present invention can be selected from commercially available products having a wide range of performance specifications, or such components can be custom manufactured for assembly into a micro atomizer according to the present invention. The orientation of components can be adjusted as well. Accordingly, these and other embodiments of the invention fall within the scope of the claims below.

What is claimed is:

1. A micro atomizer for use with a source of pressurized carrier gas and a source of liquid to be aerosolized, comprising:
   a body having a gas inlet orifice for connection to the source of pressurized carrier gas, a liquid inlet orifice for connection to the source of liquid to be aerosolized, and an outlet orifice wherein said liquid inlet orifice and said outlet orifice are aligned along a common centerline running through said body;
   a liquid inlet fitting attachable to said liquid inlet orifice of said body;
   a liquid channel in the shape of a thick-wall tube having inlet and outlet ends wherein said outlet end comprises a substantially flat top and wherein said inlet end is attachable to said liquid inlet fitting such that said inlet end of said liquid channel is in communication with said inlet orifice for connection to the source of liquid to be aerosolized and said outlet end is held substantially along the centerline of said outlet orifice of said body;
   an outlet fitting attachable to said outlet orifice of said body having a gas channel in communication with said gas inlet orifice of said body and having a tube-channel orifice for housing said liquid channel;
   a cap having an aerosol outlet orifice and an internal and external surface; and
   a cap fitting for securing said cap to said outlet fitting such that the centerline of the cap is in alignment with said common centerline running through said body whereby a liquid-gas contact space is formed by the internal surface of said cap and the substantially flat top of said outlet end of the liquid channel; and
   wherein said pressurized carrier gas and said liquid to be aerosolized are allowed to come into contact within said liquid-gas contact space to produce aerosolized liquid particles.

2. The device of claim 1, wherein said liquid channel in the shape of a thick-wall tube has an inner diameter in the range of 0.004 to 0.010 inches.

3. The device of claim 2, wherein said liquid channel in the shape of a thick-wall tube has an inner diameter of approximately 0.007 inches.

4. The device of claim 2, wherein said internal surface of said cap and said liquid channel in the shape of a thick-wall tube form a gap in communication with said gas channel of said outlet fitting through which pressurized carrier gas can flow from said gas channel into said liquid-gas contact space.

5. The device of claim 4, wherein said gap has a dimension in the range of 0.0005 to 0.0020 inches.

6. The device of claim 5, wherein said gap has a dimension of approximately 0.001 inches.

7. The device of claim 2, wherein the dimension from substantially flat top of said outlet end of the liquid channel to said aerosol outlet orifice of said cap is in the range of 0.002 to 0.008 inches.

8. The device of claim 7, wherein the dimension from said substantially flat end of said outlet end of the liquid channel in the shape of a thick-wall tube to said aerosol outlet orifice of said cap is approximately 0.005 inches.

9. The device of claim 1, wherein said micro atomizer is capable of producing stable aerosol concentrations having a mass median aerodynamic diameter (MMAD) of less than 10 microns from liquid flow rates of 10-100 microliters per hour.

\* \* \* \* \*